Figure 1:
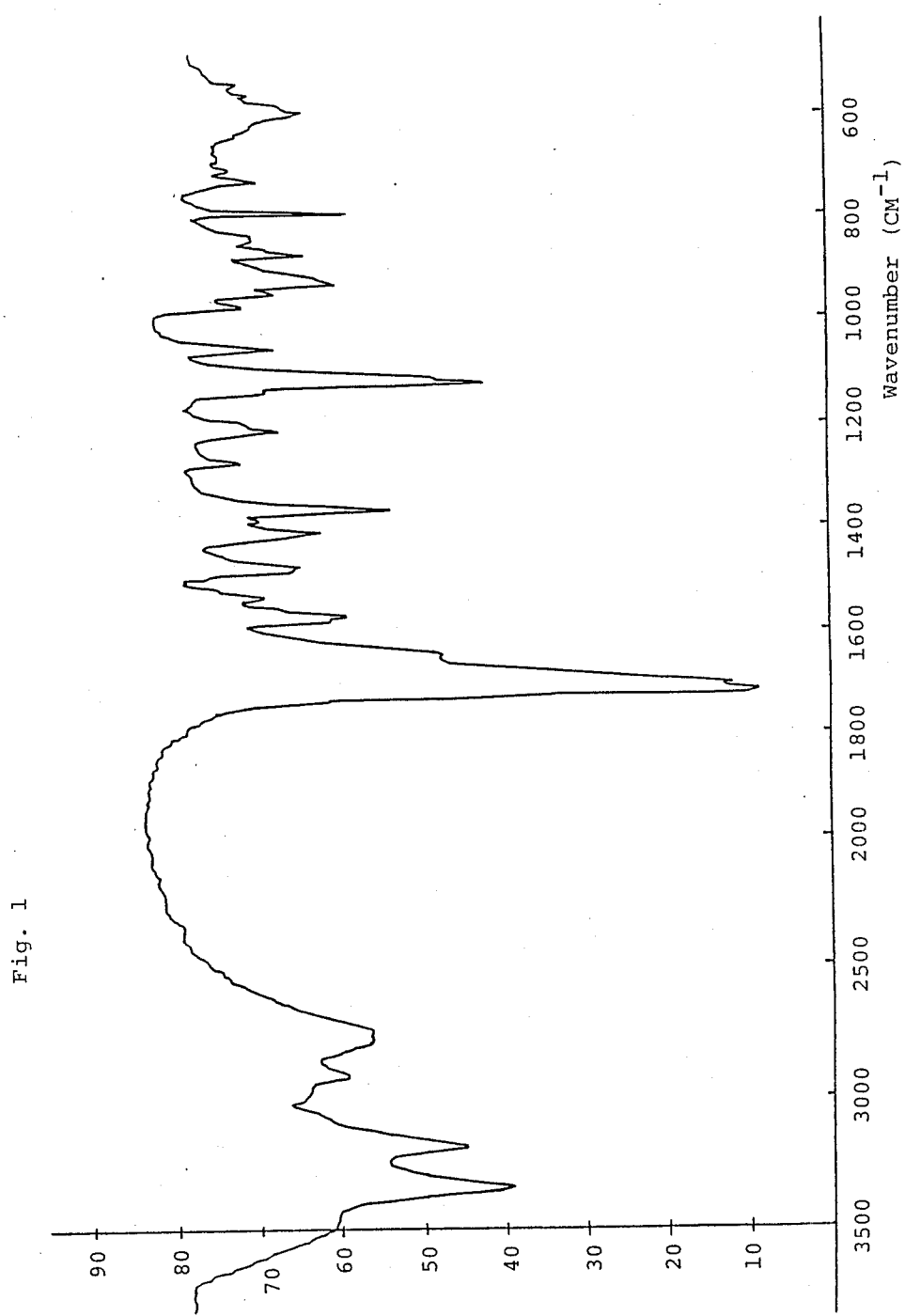

United States Patent [19]

Ishii et al.

[11] Patent Number: 4,748,176
[45] Date of Patent: May 31, 1988

[54] 7-HYDROXYGUANINE COMPOUNDS

[75] Inventors: Kiyoto Ishii, Akashi; Hajime Kawaharada, Kakogawa; Kiyoshi Watanabe, Akashi, all of Japan

[73] Assignee: Kanegafuchi Chemical Industry Co., Ltd., Osaka, Japan

[21] Appl. No.: 867,032

[22] Filed: May 27, 1986

[30] Foreign Application Priority Data

May 27, 1985 [JP] Japan .................... 60-113874

[51] Int. Cl.$^4$ .................... C07D 473/18; A61K 31/52
[52] U.S. Cl. .................... 514/262; 544/276; 544/277
[58] Field of Search ............. 544/276, 277; 514/262

[56] References Cited

U.S. PATENT DOCUMENTS 4,085,214  4/1978  Higuchi et al. ............ 514/263
4,579,849  4/1986  MacCoss et al. ........... 544/276

Primary Examiner—Nicholas S. Rizzo
Attorney, Agent, or Firm—Wegner & Bretschneider

[57] ABSTRACT

Novel 7-hydroxyguanine compounds of the formula:

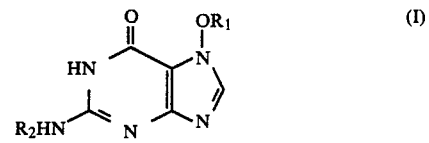

wherein R is hydrogen atom, tetrahydropyranyl group or tetrahydrofuryl group, and $R_2$ is hydrogen atom, tetrahydropyranyl group or tetrahydrofuryl group, provided that when $R_1$ is hydrogen atom, $R_2$ is tetrahydropyranyl group or tetrahydrofuryl group, and a salt thereof, which have excellent anti-tumor activity, process for preparing the compounds, and anti-tumor agent containing said compound as an active ingredient.

4 Claims, 4 Drawing Sheets

7-HYDROXYGUANINE COMPOUNDS

This invention relates to novel 7-hydroxyguanine compounds and a salt thereof, a process for preparing the compounds, and an anti-tumor agent containing the compound as an active ingredient. More particularly, it relates to novel 7-hydroxyguanine compounds of the formula:

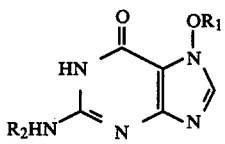

(I)

wherein $R_1$ is hydrogen atom, tetrahydropyranyl group or tetrahydrofuryl group, $R_2$ is hydrogen atom, tetrahydropyranyl group or tetrahydrofuryl group, provided that when $R_1$ is hydrogen atom, $R_2$ is tetrahydropyranyl group or tetrahydrofuryl group, and a salt thereof with a compound being capable of producing a salt with said compounds, a process for preparing the compounds, and an anti-tumor agent or composition containing the compound as an active ingredient.

The present inventors have prepared various derivatives by chemical modification of 7-hydroxyguanine of the formula:

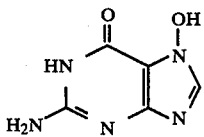

(II)

and have studied the pharamacological activities thereof, and then have found that the compounds of the above formula (I) and a salt thereof have excellent anti-tumor activity.

The compounds of the formula (I) are all amphoteric compounds and can form a salt with a base or acid, and the salts of the compounds (I) in the present invention include salts with a compound being capable of forming a salt therewith. Suitable examples of the salts with a base are (i) salts with alkali metals or alkaline earth metals, (ii) ammonium salt, (iii) salts with amines, particularly with ethylamine, dimethylamine, piperidine, morpholine, etc. Suitable examples of the salts with an acid are (i) salts with mineral acids, particularly, hydrochloride, hydroiodide, or sulfate, (ii) salts with organic acids, particularly benzenesulfonate, p-toluenesulfonate, naphthalenesulfonate, acetate, propionate, citrate, malonate, etc. These salts are preferably a pharmacologically acceptable salt in order to use the compounds as an anti-tumor agent.

Particularly suitable examples of the compounds in the present invention are shown in the following Table 1.

TABLE 1

Figure 2:
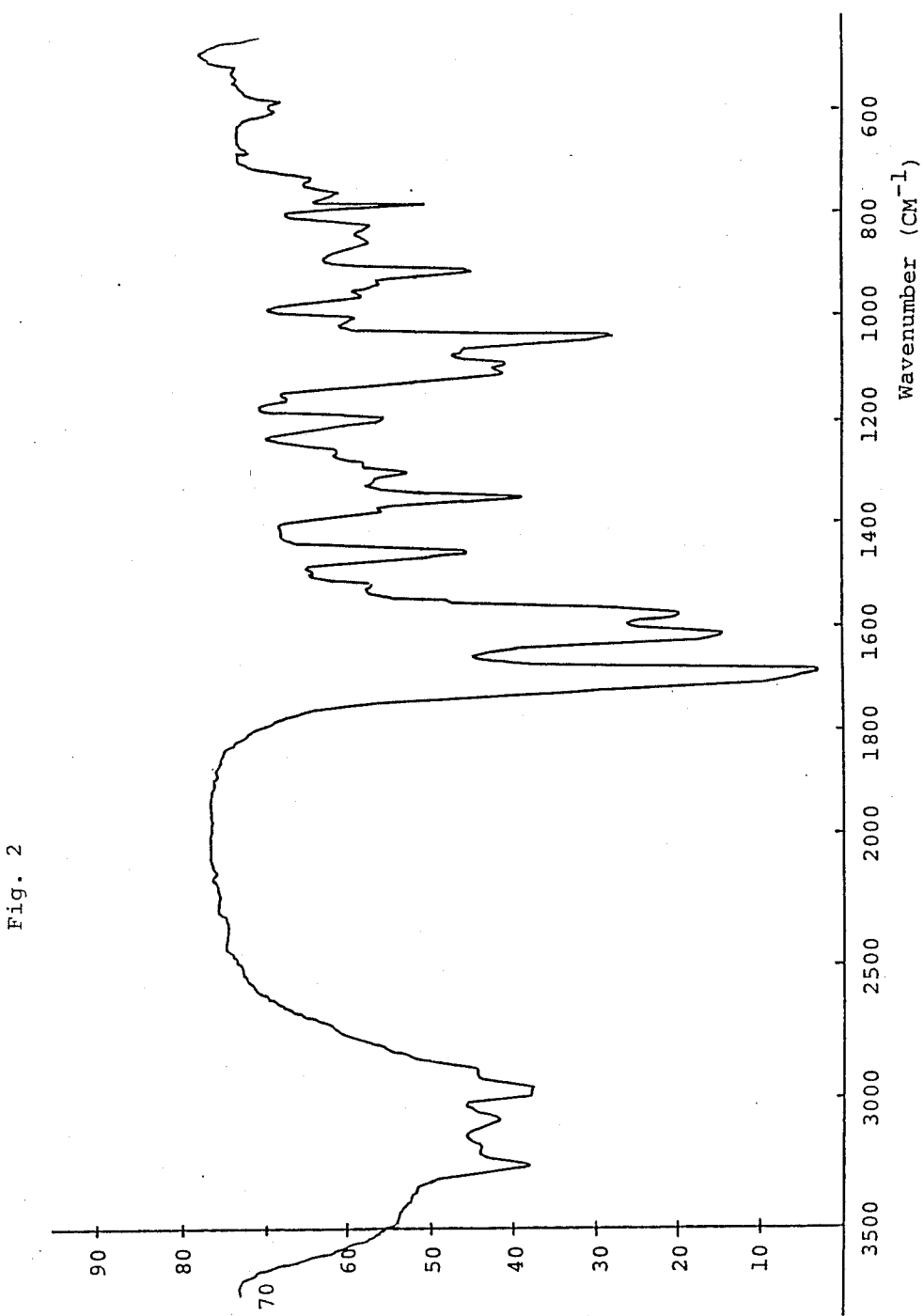
Figure 3:
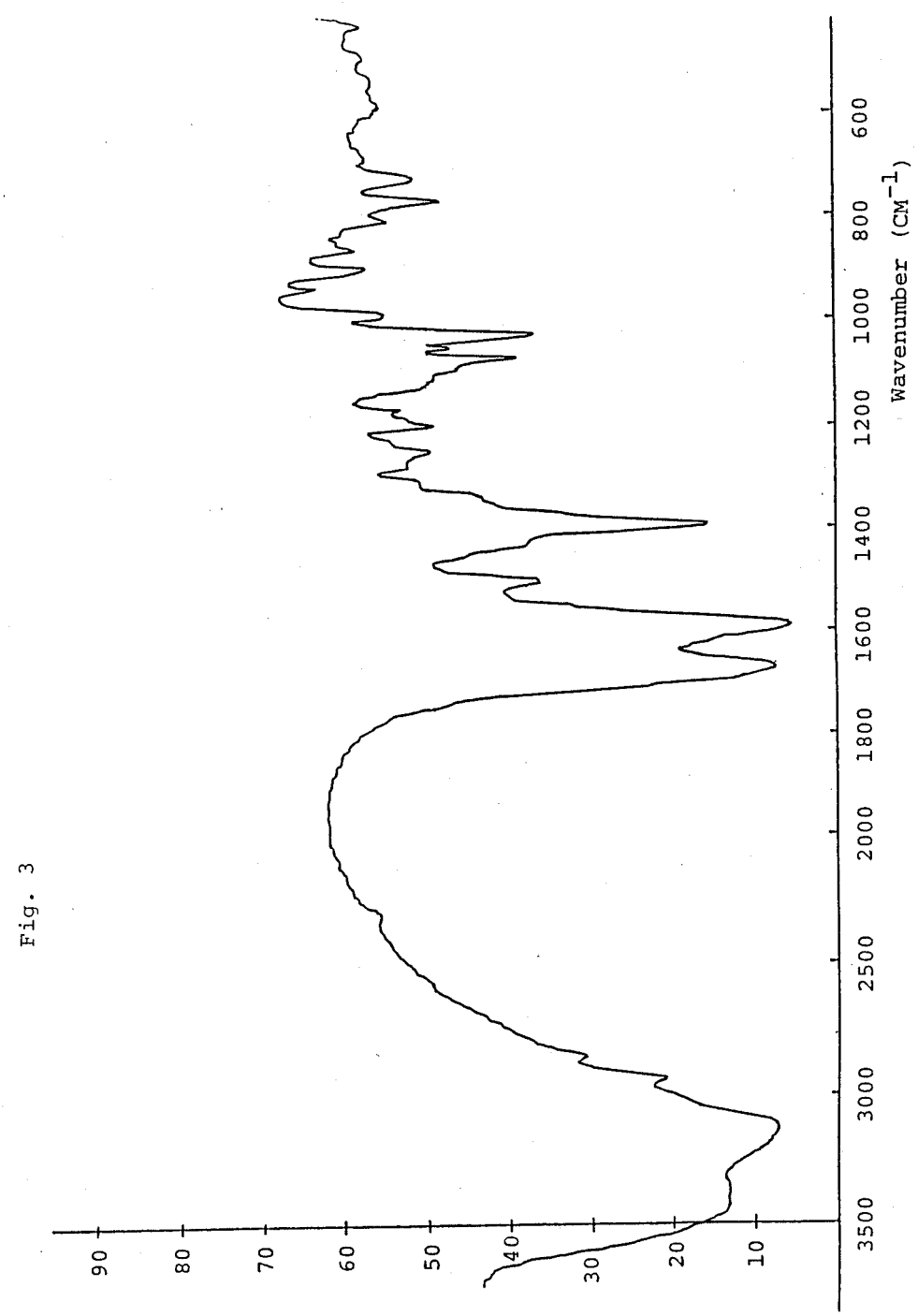
Figure 4:
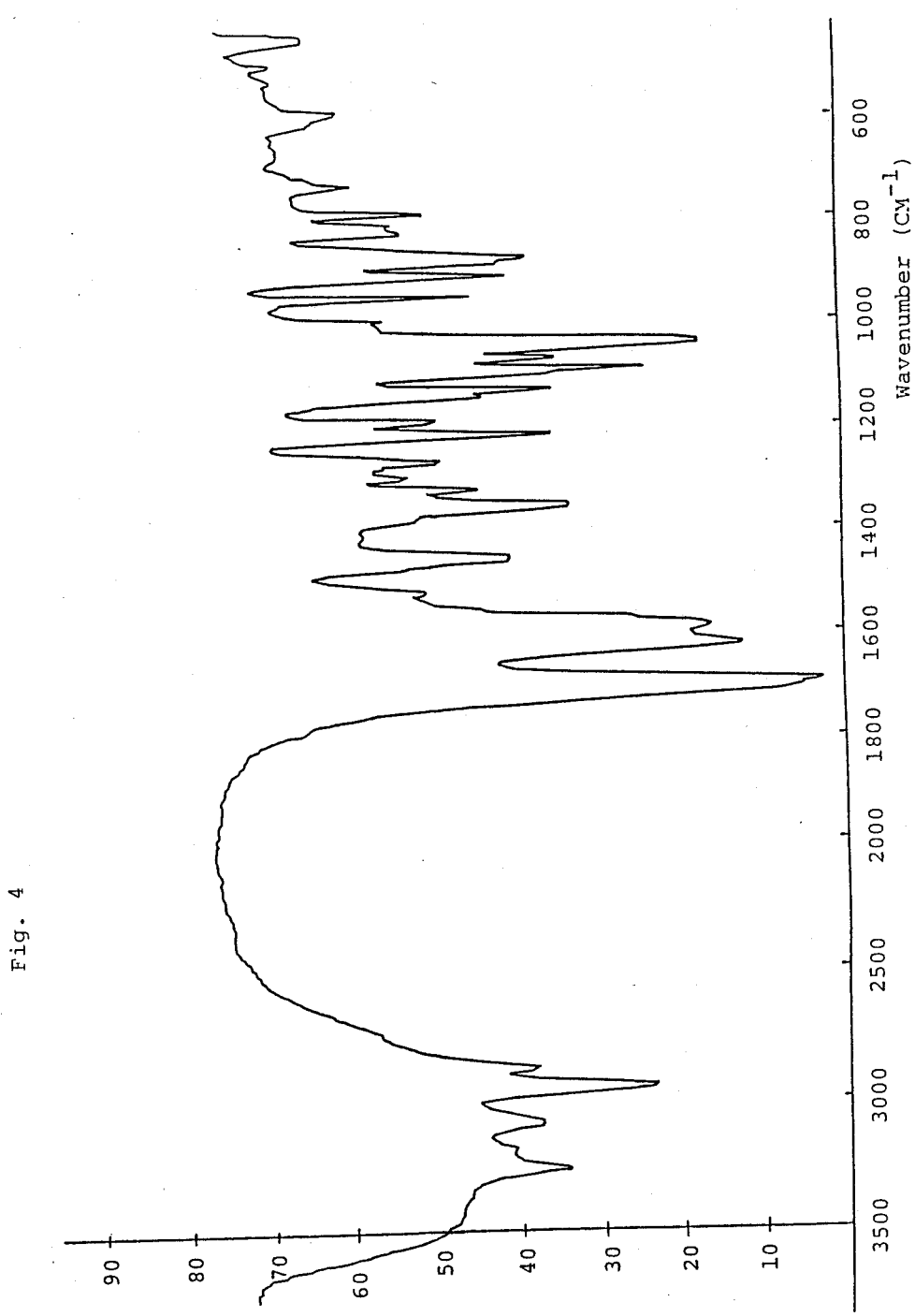

| No. | | Compound 1 | Compound 2 | Compound 3 | Compound 4 |
|---|---|---|---|---|---|
| $R_1$ | | THF | THF | H | THP |
| $R_2$ | | H | THF | THP | THP |
| Form | | White powder | White powder | White powder | White powder |
| Melting point | | 124–130 (dec.) | 244–260 (dec.) | 184–190 (dec.) | 108–112 (dec.) |
| Molecular weight | | 237 | 307 | 251 | 337 |
| Molecular formula | | $C_9H_{11}N_5O_3$ | $C_{13}H_{17}N_5O_4$ | $C_{10}H_{13}N_5O_3$ | $C_{15}H_{23}N_5O_4$ |
| Elementary analysis | | | | | |
| Found | C | 45.62 | 50.65 | 47.80 | 53.29 |
| | H | 4.69 | 5.64 | 5.24 | 6.95 |
| | N | 29.33 | 22.63 | 27.81 | 20.66 |
| Calcd. | C | 45.57 | 50.81 | 47.80 | 53.40 |
| | H | 4.67 | 5.58 | 5.22 | 6.87 |
| | N | 29.53 | 22.79 | 27.88 | 20.76 |
| UV spectrum $\lambda_{max}^{MeOH}$ nm($\epsilon \times 10^4$) | | 215(2.02) 244(0.62) 288(0.68) | 216(4.67) 247(1.58) 288(1.47) | 215(1.87) 237(0.86) 285(0.68) | 215(3.94) 246(1.35) 285(1.28) |
| IR spectrum (KBr) | | FIG. 1 | FIG. 2 | FIG. 3 | FIG. 4 |

The compounds (I) of the present invention can be prepared as follows.

The starting 7-hydroxyguanine (II) can be prepared from the culture broth of Streptomyces sp. by a method as described in Preparation hereinafter.

The compounds (I) of the present invention can be prepared by reacting 7-hydroxyguanine (II) or a salt thereof with 2,3-dihydropyrane or 2,3-dihydrofuran in a polar aprotic solvent (e.g. dimethylsulfoxide, dimethylformamide, etc.) in the presence of an acid catalyst (e.g. hydrochloric acid, sulfuric acid, etc.). The compound (I) thus obtained can easily be isolated from the reaction mixture by distilling off the solvent to obtain the residue or precipitating the product by adding a low polar solvent to the reaction mixture, and subjecting the residue or precipitate thus obtained to conventional silica gel column chromatography or separatory thin layer chromatography or by repeating these treatment, by which the desired compounds can be obtained in high purity.

The compounds (I) or a salt thereof of this invention show excellent anti-tumor activities against various tumors such as Hodgkin's disease, reticulosarcoma, leukemia, multiple myeloma, deciduocellular sarcoma, lung cancer, mammary cancer, ovary cancer, uterine cancer, stomach cancer, hepatic cancer, skin cancer, and the like. The representative anti-tumor activity is illustrated by the following experiment.

EXPERIMENT 1: ANTI-TUMOR ACTIVITY AGAINST L-1210 LEUKEMIA IN MICE $BDF_1$ female mice weighing 18–23 g (one group: 3 mice) were used. The mice were intraperitoneally inoculated with mouse L-1210 leukemia cells ($1 \times 10^5$). From the next day after inoculation of leukemia cells, a solution or suspension of a test compound in 50 mM phosphate buffer (pH 7.4) was intraperitoneally administered for 5 days in a dose as shown in Table 2, and the survival days of mice was measured. As a control, 50 mM phosphate buffer (pH 7.4) without a test compound was intraperitoneally administered likewise. Based on the data, the life-prolongation ratio of the test compound was calculated. The results are shown in Table 2.

TABLE 2

| Dose (mg/kg/day) | Life-prolongation ratio* | | | |
|---|---|---|---|---|
| | Compound 1 | Compound 2 | Compound 3 | Compound 4 |
| 4.0 | 133.8 | 103.4 | 141.3 | 104.8 |
| 16.0 | 150.0 | 130.0 | 146.3 | 122.0 |
| 32.0 | 133.8 | 137.9 | 160.2 | 138.4 |

*Life-prolongation ratio (%) = $\dfrac{\text{Average survival days of treated mice}}{\text{Average survival days of untreated mice}} \times 100$ The test compounds shown in Table 2 correspond to those in Table 1.

As is clear from the experimental results in Table 2, the compounds of this invention show excellent anti-tumor activity.

EXPERIMENT 2: ACUTE TOXICITY

ICR male mice weighing 18–23 g were intraperitoneally administered with the test compounds for one week, and the 50% lethal toxicity ($LD_{50}$: mg/kg) was measured by a conventional method. As a result, all Compounds 1, 2, 3 and 4 showed $LD_{50}$ in the range of 160.0 to 320 mg/kg.

The compounds (I) or a pharmaceutically acceptable salt thereof can be used as an anti-tumor agent for the prophylaxis or treatment of tumors in animals including human being. The compounds (I) or a salt thereof are usually used in the form of a pharmaceutical composition. The composition includes conventional pharmaceutical preparations, for example, solid preparations such as tablets, pills, capsules, granules, fine granules, powders, etc. and liquid preparations such as solutions, suspensions, injections. The compositions can be prepared by admixing the active compound (I) or a pharmaceutically acceptable salt thereof with a conventional pharmaceutically acceptable carrier or diluent in a usual manner. The pharmaceutically acceptable carriers or diluents used from the oral preparations include, for example, binding agents (e.g. syrup, gum arabic, gelatine, sorbitol, tragacanth, polyvinylpyrrolidone, etc.), excipients (e.g. lactose, sucrose, corn starch, potassium phosphate, sorbitol, etc.), lubricants (e.g. magnesium stearate, talc, polyethylene glycol, silica, etc.), disintegrators (e.g. potato starch, etc.), wetting agents (e.g. sodium laurylsulfate, etc.). For parenteral administration, they may be used in the form of an injection, solution, suspension, or emulsion in admixture with conventional pharmaceutically acceptable carrier or diluents suitable for the parenteral administration, such as physiological saline solution, glycerin, propylene glycol, simple syrup, ethanol, fatty oils, ethylene glycol, sorbitol, or the like. The pharmaceutical compositions contains the active compound (I) or a salt thereof in an amount of 40 to 800 mg, preferably 20 to 200 mg, in a dosage unit and may also contain other medicaments than the active compounds (I) or a salt thereof.

The compositions of this invention can be administered in oral or parenteral route.

The compounds (I) or a salt thereof of this invention are used in a dose effective for the prophylaxis or treatment of tumors without undesirable side effect. The dose may vary depending on the age, weight and sex of patient, administration route, severity of disease, and the like, and the most effective dose may be decided by doctors, but it is usually in a range of 40 to 800 mg per day in adult.

The present invention is illustrated by the following Preparation and Examples, but should not be construed to be limited thereof.

PREPARATION 1

Preparation of Substrate (7-Hydroxyguanine)

Streptomyoee sp. A-347 strain (which has been deposited as FERM BP-541 at Fermentation Research Institute, Agency of Industrial Science and Technology, Japan under Budapest Treaty) which is previously cultured on a slant agar medium is inoculated into a 500 ml flask which contains a liquid medium (pH 7.4, 100 ml) containing glucose 2.0%, sucrose 1.0%, soy bean powder 2.0% and calcium carbonate 0.3%, and it is cultured on a rotary shaking machine at 28° C. for 48 hours to give a seed liquid culture.

180 ml of the seed liquid culture obtained above is inoculated into a 30 liter jar fermentor containing the same liquid medium as above (18 liter), and it is cultured at 28° C. for 90 hours (agitation speed: 350 r.p.m., aeration volume: 9 liter/minute). The cultures obtained in two fermentors are combined and regulated to pH 3.2 with 5N hydrochloric acid, and then centrifuged to give a culture filtrate. The filtrate is regulated to pH 5.2 with 5N sodium hydroxide solution (volume: 27.5 liter, content of the compound: 100 μg/ml). The culture filtrate (27.5 liter) is passed through a column (8.4 cm×60 cm) packed with Amberlyst ® 15 ($H^+$ type) (4.0 liter) to adsorb the compound thereto. The column is washed with water (8 liter) and eluted with 0.5N aqueous ammonia to give an eluate fraction containing the compound (8 liter). This fraction is concentrated under reduced pressure to remove ammonia, and thereto is added deionized water so as to make totally 15 liter (content of the compound: 158 μg/ml).

The solution (15 liter) obtained above is passed through a column (6 cm×35 cm) packed with Amberlite ® IRA-45 ($OH^-$ type) (1 liter) to adsorb the compound, and the column is eluted with 0.3N aqueous ammonia to give an active fraction (1 liter). This fraction is concentrated under reduced pressure to remove ammonia and thereto is added deionized water so as to make totally 3 liter (content of the compound: 700 μg/ml).

The solution (3 liter) thus obtained is subjected to ion exchange chromatography using a column (inner diameter: 3 cm, volume: 300 ml) packed with DEAE-Sephade ® A-25 ($HCO_3^-$ type), and the column is washed with 0.05M aqueous ammonium bicarbonate (300 ml) and then eluted with 0.2M aqueous ammonium bicarbonate to give fractions (each 10 ml). The 50th to 95th fractions are combined and concentrated under reduced pressure at 60° C. to precipitate crude powder of 7-hydroxyguanine (1412 mg, 991 μg/ml). The crude powder of 7-hydroxyguanine (1035 mg) is dissolved in 5N aqueous ammonia (45 ml) at 60° C., and the mixture is allowed to stand in cooled place (5° C.) overnight. The precipitated crystals are separated by filtration to give pure 7-hydroxyguanine (636.3 mg, 1,000 μg/ml) as plates.

m.p. >300° C.

Molecular weight: 167 (FD-MS, m/z 167; $M^+$)

Elementary analysis for $C_5H_5N_5O_2$:
Calcd. (%): C,35.95; H,3.02; N,41.90.
Found (%): C,35.08; H,3.10; N,40.92.

EXAMPLE 1

7-Hydroxyguanine [Compound (II)] (2 g) is suspended in dimethylsulfoxide (50 ml), and thereto is added a separately prepared 6.0M hydrochloric acid-containing dioxane (3 ml), and the mixture is stirred for 10 minutes. To the resulting clear reaction mixture is added 2,3-dihydrofuran (1.9 ml), and the mixture is reacted under argone for 50 minutes The reaction mixture is neutralized by adding thereto sodium bicarbonate (2 g), and the mixture is entered into ice water (2 liter). The solution is extracted with ethyl acetate (500 ml) to remove the byproducts. The remaining solution (1.9 liter) is allowed to stand at 4° C. overnight. The resulting precipitate is collected by filtrated and dried under reduced pressure to give a crude powder of Compound (1) (1.22 g). The crude product is subjected to a column chromatography with silica gel (Wako GEL ® C-200, manufactured by Wako Junyaku, 200 ml), being developed by chloroform-methanol (10:1 by volume). The eluate fractions (300 ml to 600 ml) are collected and concentrated to give pure white powder (832 mg) of the desired Compound 1.

m.p. 124°–130° C. (dec.)
Elementary analysis for $C_9H_{11}N_5O_3$:
Calcd. (%): C,45.57; H,4.67; N,29.53.
Found (%): C,45.62; H,4.69; N,29.33.
IR spectrum is as shown in FIG. 1.
$^1$H-NMR (DMSO-D$_6$) $\delta$ppm: 10.85 (s, 1H), 8.03 (s, 1H), 6.15 (s, 2H), 5.79 (s, 1H), 3.5–4.2 (m, 2H), 1.7–2.2 (m, 4H)
Silica gel TLC [F$_{254}$ Art5715, manufacatured by Merck Co.; developer: chloroform-methanol (4:1 by volume)]: Rf value 0.50

EXAMPLE 2

7-Hydroxyguanine [Compound (II)] (500 mg) is suspended in dimethylsulfoxide (25 ml), and thereto is added a separately prepared 6.0 μM hydrochloric acid-containing dioxane (1 ml), and the mixture is stirred for 10 minutes. To the reaction mixture is added 2,3-dihydrofuran (1.17 ml), and the mixture is stirred under argone for 30 minutes. The reaction mixture is regulated to pH 7.4 by adding thereto sodium bicarbonate (600 mg). The reaction mixture is entered into 5% aqueous ammonium bicarbonate solution (500 ml), and the solution is extract with ethyl acetate (800 ml). The extract is dehydrated with anhydrous sodium sulfate, and then concentrated under reduced pressure to give a gummy substance (548 mg). The gummy substance is subjected to a column chromatography with silica gel (Wako gel ® C-200, manufactured by Wako Junyaku, 100 ml). After washing with chloroform (500 ml), it is developed by chloroform-methanol (50:1 by volume). The eluate fractions (970 ml to 980 ml) are collected and concentrated to give pure white powder (102.6 mg) of the desired Compodnd 2.

m.p. 244°–260° C. (dec.)
Elementary analysis for $C_{13}H_{17}N_5O_4$:
Calcd. (%): C,50.81; H,5.58; N,22.79.
Found (%): C,50.65; H,5.64; N,22.63.
IR spectrum is as shown in FIG. 2.
$^1$H-NMR (CDCl$_3$) $\delta$ppm: 7.70 (s, 1H), 5.84 (s, 1H), 5.03 (s, 1H), 3.2–4.3 (4H), 1.3–2.5 (8H)

Silica gel TLC [F$_{254}$, manufacatured by Merck Co.; developer: chloroform-methanol (9:1 by volume)]: Rf value 0.47

EXAMPLE 3

7-Hydroxyguanine [Compound (II)] (1000 mg) is suspended in dimethylsulfoxide (25 ml), and thereto is added a separately prepared 6.0M hydrochloric acid-containing dioxane (2.0 ml), and the mixture is stirred for 10 minutes. To the resulting clear reaction mixture is added 2,3-dihydropyran (1.12 ml), and the mixture is stirred under argone for 4 hours. The reaction mixture is neutralized by adding thereto sodium bicarbonate (1200 mg). To the mixture are added ethyl acetate (250 ml) and n-hexane (250 ml), and the resulting precipitates are taken by filtration and dried under reduced pressure to give yellow powder. The yellow powder is purified by subjecting to a column chromatography with silica gel (Wako gel ® C-200, manufactured by Wako Junyaku, 150 ml) to give pure powder (270 mg) of the desired Compound 3.

m.p. 184°–190° C. (dec.)
Elementary analysis for $C_{10}H_{13}N_5O_3$:
Calcd. (%) C,47.80; H,5.22; N,27.88.
Found (%): C,47.80; H,5.24; N,27.81.
IR spectrum is as shown in FIG. 3.
$^1$H-NMR (DMSO-d$_6$) $\delta$ppm: 7.95 (s, 1H), 6.74 (d, 1H), 5.02 (t, 1H), 3.2–3.8 (m, 2H), 1.2–1.8 (m, 6H)
Silica gel TLC [F$_{254}$, manufacatured by Merck Co.; developer: chloroform-methanol-water (78:20:2 by volume)]: Rf value 0.14

EXAMPLE 4

7-Hydroxyguanine [Compound (II)] (3.0 g) is suspended in dimethylsulfoxide (60 ml), and thereto is added a separately prepared 6.0M hydrochloric acid-containing dioxane (6.0 ml), and the mixture is stirred for 10 minutes. To the resulting mixture is added 2,3-dihydropyran (16.8 ml), and the mixture is stirred under argone for 45 minutes. To the reaction mixture is added sodium bicarbonate (3.1 g). After completion of the reaction, to the reaction mixture are added dichloromethane (500 ml) and n-hexane (700 ml), and the resulting precipitates are filtered off, and the filtrate is passed through a silica gel column (Wako gel ® C-200, manufactured by Wako Junyaku, 400 ml). The passed through solution is concentrated. The resulting oily substance (1.78 g) is subjected to a column chromatography with silica gel (Wako gel ® C-200, manufactured by Wako Junyaku, 150 ml). After washing with chloroform (1 liter), it is developed by chloroform-methanol (50:1 by volume). The eluate fractions (128 ml to 150 ml) are collected and concentrated to give pure white powder (182 mg) of the desired Compound 4.

m.p. 108°–112° C. (dec.)
Elementary analysis for $C_{15}H_{23}N_5O_4$: Calcd. (%): C,53.40; H,6.87; N,20.76. Found (%): C,53.29; H,6.95; N,20.66.
IR spectrum is as shown in FIG. 4.
$^1$H-NMR (CDCl$_3$) $\delta$ppm: 11.32 (broad s, 1H), 8.40 (m, 1H), 7.72 (s, 1H), 5.43 (s, 1H), 5.18 (t, 1H), 3.4–4.2 (m, 4H), 1.3–2.2 (m, 12H) Silica gel TLC [developer: chloroform-methanol (9:1 by volume)]: Rf value 0.53

What is claimed is:
1. A 7-hydroxyguanine compound of the formula:

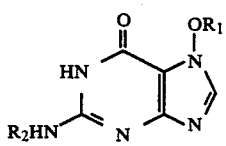

wherein $R_1$ is hydrogen atom, tetrahydropyranyl group or tetrahydrofuryl group, $R_2$ is hydrogen atom, tetrahydropyranyl group or tetrahydrofuryl group, provided that when $R_1$ is hydrogen atom, $R_2$ is tetrahydropyranyl group or tetrahydrofuryl group, or a pharmaceutically acceptable salt thereof.

2. The compound according to claim 1, wherein $R_1$ is tetrahydrofuryl group and $R_2$ is hydrogen atom.

3. The compound according to claim 1, wherein $R_1$ is hydrogen atom and $R_2$ is tetrahydropyranyl group.

4. A antitumor composition which comprises as an active ingredient an effective amount of a 7-hydroxyguanine compound of the formula:

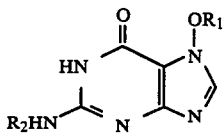

wherein $R_1$ is hydrogen atom, tetrahydropyranyl group or tetrahydrofuryl group, and $R_2$ is hydrogen atom, tetrahydropyranyl group or tetrahydrofuryl group, provided that when $R_1$ is hydrogen atom, $R_2$ is tetrahydropyranyl group or tetrahydrofuryl group, or a pharmaceutically acceptable salt thereof in admixture with a pharmaceutically acceptable carrier or diluent.

* * * * *